United States Patent
Navarrini et al.

(10) Patent No.: US 6,747,109 B2
(45) Date of Patent: Jun. 8, 2004

(54) PERFLUORODIACYLPEROXIDES AS POLYMERIZATION INITIATORS

(75) Inventors: Walter Navarrini, Milan (IT); Marco Galimberti, Milan (IT)

(73) Assignee: Solvay Solexis S.p.A, Milan (IT)

( * ) Notice: Subject to any disclaimer, the term of this patent is extended or adjusted under 35 U.S.C. 154(b) by 0 days.

(21) Appl. No.: 10/086,844

(22) Filed: Mar. 4, 2002

(65) Prior Publication Data

US 2002/0128411 A1 Sep. 12, 2002

(30) Foreign Application Priority Data

Mar. 8, 2001 (IT) ..................... MI2001A0482

(51) Int. Cl.$^7$ ................................. C08F 4/32
(52) U.S. Cl. .............. 526/227; 526/231; 526/255
(58) Field of Search ................. 526/227, 231, 526/255

(56) References Cited

U.S. PATENT DOCUMENTS

| | | | |
|---|---|---|---|
| 3,671,510 A | 6/1972 | Kometani et al. | |
| 4,846,006 A | 7/1989 | Thibeault | 73/865.9 |
| 4,864,006 A | 9/1989 | Giannetti et al. | 526/209 |
| 4,897,457 A | * 1/1990 | Nakamura et al. | 526/247 |
| 4,910,276 A | * 3/1990 | Nakamura et al. | 526/247 |

FOREIGN PATENT DOCUMENTS

| | | |
|---|---|---|
| EP | 0 606 492 A1 | 7/1994 |
| GB | 781532 | 8/1957 |
| WO | WO 91/00272 | 10/1991 |
| WO | 97/08142 | 3/1997 |
| WO | WO 01/16100 | 8/2001 |

OTHER PUBLICATIONS

H. Sawada; Chem. Rev., vol. 96, pp. 1779–1808 (1996); "Fluorinated Peroxides".

Sawada et al.; Chemical Abstracts, vol. 112: 117996b; 1989 "Hydrolysis of bis(perfluoroalkanoyl) peroxides".

* cited by examiner

Primary Examiner—Bernard Lipman
(74) Attorney, Agent, or Firm—Arent Fox PLLC

(57) ABSTRACT

Perfluorodiacylperoxides having the following structures:

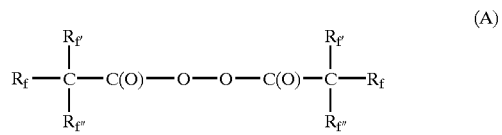

(A)

wherein:

when $R_f$ is F, $R_{f'}$, $R_{f''}$ are both —$CF_3$;

when $R_f$ is —$CF_3$, $R_{f'}$, $R_{f''}$ are $C_1$–$C_3$ linear or branched perfluorooxyalkyl groups;

said perfluorodiacylperoxides being such as to meet the following proviso: the thermal decomposition constants $K_d$ (sec$^{-1}$) in the presence of water do not undergo substantial variations with respect to the thermal decomposition constants in absence of water.

14 Claims, No Drawings

PERFLUORODIACYLPEROXIDES AS POLYMERIZATION INITIATORS

The invention relates to perfluorodiacylperoxides used as polymerization initiators in a wide temperature range.

Specifically the invention relates to perfluorodiacylperoxides obtainable with good yields from the respective perfluoroacyifluorides and having a high hydrolytic stability, in particular when used as polymerization initiators in aqueous medium. The high hydrolytic stability of said initiators confers to the polymerization process improved yields while the perfluorinated structure of the initiator allows to obtain polymers having stable perfluoroalkyl end groups.

The use as polymerization initiators of halogenated diacylperoxides is known in the prior art. These compounds can be obtained by synthesis from the respective acyl-halides, using various methods described in the literature. The perfluorodiacylperoxide synthesis from the respective perfluoro-acyl-halides in the presence of $H_2O_2$ and NaOH is described, for example, by H. Sawada in Chemical Review, 1996, Vol. 96, 1779–1808. In the prior art to synthesize perfluorodiacylperoxides, perfluoroacylchlorides are preferably used since they are more reactive than the corresponding perfluoroacylfluorides. In fact, perfluoroacylfluorides determine lower synthesis yields than the corresponding chlorides. Besides, the obtained perfluorodiacylperoxides cause secondary reactions since they are easily hydrolyzed by the reaction medium wherein they are produced.

The perfluorodiacylperoxides exemplified in the prior art as polymerization initiators give low yields when used in polymerization processes in aqueous medium. To overcome this drawback one can polymerize in the presence of solvent. However the polymerization in solvent is more expensive than that in aqueous medium. Besides, it is necessary to use particular solvents which have no environmental impact, otherwise supplementary units would be necessary for their treatment. Besides, the polymerization in aqueous medium allows to generally obtain higher polymerization yields and a better control of the molecular weights of the polymers.

From the industrial point of view it is therefore advantageous to polymerize in aqueous medium using initiators which are not hydrolyzed in the reaction medium. On the other hand non fluorinated initiators are known, for example ammonium persulphate, which have a good hydrolytic stability, thus allowing the water polymerization with good yields. However these initiators have the drawback to lead to the obtainment of polymers having unstable end groups and therefore unusable in applications where a high stability and a high purity degree of the final polymer are required, for example in optical applications. For these uses it would be necessary to treat them to obtain stable end groups.

In GB 781,532 it is described the polymerization of perfluoro-olefins using perfluorinated or chlorofluorinated solvents in the presence of initiators. In said patent it is pointed out how the use of perfluorinated peroxides as polymerization initiators in aqueous medium is not possible since the presence of water determines the deactivation of the peroxide itself already at temperatures higher than 0° C.

U.S. Pat. No. 3,671,510 points out how the perfluorodiacylperoxides are hydrolyzed in the presence of water, wherefore the initiator efficiency is strongly compromised and therefore the monomer conversion is notably reduced. To overcome these inconveniences, this patent suggests the use of (perchlorofluoro)-di-acylperoxides as polymerization initiators in aqueous medium. However, the use of said peroxides implies the drawback to give polymers having unstable end groups with the above disadvantages.

EP 606,492 refers to a polymerization process in aqueous phase of tetrafluoroethylene with hexafluoropropene, wherein difluoroacylperoxides are used as polymerization initiators in the presence of suitable perfluoroalkylcarboxylic acids. Said perfluoroalkylcarboxylic acids decrease the tendency to hydrolysis of perfluoroacylperoxides. However, by operating in acid medium there is the drawback to have a poor stability of the obtained polymer latex.

The easiness to hydrolysis of perfluorodiacylperoxides is more stressed for the compounds having a low molecular weight, see Sawada et al in Chem. Abs. Vol. 112:117996b and patent application WO 97/08142. Said patent application describes a synthesis method to limit the tendency to hydrolysis of the obtained perfluorodiacylperoxides. The process variables, for example reaction temperature, contact time among reactants, mixing and ratio among reactants, must be very carefully determined and strictly maintained constant during the process. To maintain these variables in the narrow range useful to avoid hydrolysis, one uses complicated equipments, as ultrasound systems or microejectors The drawback of the described process resides in that it is difficult to bring it on an industrial scale.

The Applicant has surprisingly found perfluorodiacylperoxides having end groups with branched or cyclic structure, which are not hydrolyzed in aqueous medium for long times at the corresponding temperatures of thermal decomposition. Depending on their decomposition temperature they are usable as polymerization initiators in a wide temperature range, from −20° C. to 100° C., and they allow to obtain improved yields (see the comparative Examples).

An object of the present invention are therefore perfluorodiacylperoxides having the following structures:

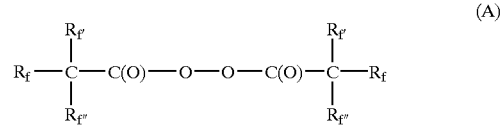

(A)

wherein:
when $R_f$ is F, $R_{f'}$, $R_{f''}$ are both —$CF_3$;
when $R_f$ is —$CF_3R_{f'}$, $R_{f''}$ are $C_1$–$C_3$ linear or branched perfluorooxyalkyl groups;

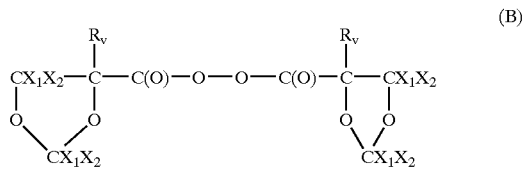

(B)

wherein:
$R_v$ is selected from F, perfluorooxyalkyl, $C_1$–$C_3$ linear or branched perfluoroalkyl;
$X_1$, $X_2$ are selected from F, perfluoroalkyl, $C_1$–$C_3$ linear or branched perfluorooxyalkyl.

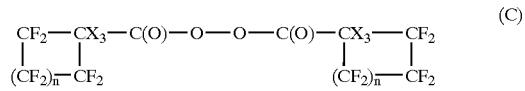

(C)

wherein: p1 n=1–3
$X_3$ is selected from F, $C_1$–$C_3$ linear or branched perfluoroalkyl, with the proviso that for n=3, $X_3$ cannot be F; said perfluorodiacylperoxides meet the following condition: the thermal decomposition constants $K_d$ (sec$^{-1}$) in the presence of water do not undergo substantial variations with respect to the thermal decomposition constants in absence of water.

This means that the perfluorodiacylperoxides of the invention can be used as initiators in aqueous polymerization without any variation of the half-life times determined under anhydrous conditions. Therefore the invention compounds can be used also after storage in aqueous emulsion for long times, even over 2–3 days, without undergoing any hydrolytic decomposition. This represents a further advantage from the industrial point of view since there is no need of immediate use of the acylperoxide differently from what happens for the acylperoxides known in the prior art.

The perfluorodiacylproxides of the invention are obtained by synthesis of the corresponding perfluoroacylhalides in the presence of $H_2O_2$ and NaOH. In particular, they can be prepared by addition of perfluoroacylfluorides to a biphase system formed by a halogenated solvent and by an aqueous solution containing $H_2O_2$ and an alkaline metal hydroxide, such as for example NaOH, KOH. The halogenated solvent can be 1,1,2-trichloro-1,2,2-trifluorethane, trichlorofluoromethane, perfluoroheptane, perfluoropolyethers. The fed amounts of perfluoracylfluoride range from 0.5 to 2 moles per mole of $H_2O_2$; the amount of alkaline metal hydroxide is in the range 0.8–1.5 moles per mole of perfluoroacylfluoride. The system is maintained under stirring in a temperature range from –15° C. to 20° C., preferably from –5° C. to +5° C. The organic phase containing the reaction products in solution is recovered from the aqueous phase by separation. A washing step with water of the organic phase and subsequent anhydrification with sodium sulphate follows.

A further object of the present invention is a polymerization process in solvent or in aqueous medium of one or more fluorinated monomers wherein as polymerization initiators the above perfluorodiacylperoxides are used.

As polymerization solvents, fluorinated solvents, preferably (per)fluoroalkanes or (per)fluoropolyethers are used.

As said the compounds of the invention can be used in a wide temperature range depending on the polymerization type. This is possible since the perfluorodiacylperoxides of the invention decompose in a surprisingly wide temperature range. For example, in the preparation of vinylidene fluoride (VDF)-based polymers it is preferable to use low polymrization temperatures (0°–10° C.). Viceversa, in the case of copolymers having a high content of not very reactive mono-mers, as in the case of copolymers of 2,2,3-trifluoro-4-tri-fluoromethoxy-1,3-dioxole (TTD), it is preferable to carry out the polymerization at higher temperatures (higher than 50° C.).

In particular for the polymerization reactions at temperatures of the order of 50°–80° C., the compounds of structure (C) or the compound of structure (A) having the formula:

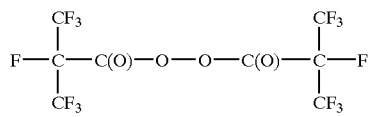

are preferably used.

For the polymerization ractions at low temperature, of the order of –20°–+25° C., the compounds of structure (A) of formula:

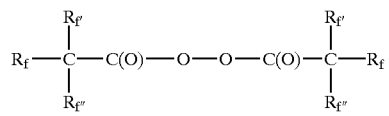

are preferably used, wherein when $R_f$ is —$CF_3$, $R_{f'}$ and $R_{f''}$ are $C_1$–$C_3$ linear or branched perfluorooxyalkyl groups. Said acylperoxides of group (A) can furthermore be used as polymerization initiators in solvent at a temperature lower than 0° C.

As fluorinated monomers polymerizable in the presence of the perfluorodiacylperoxides of the invention, we can mention:

$C_2$–$C_8$ perfluoroolefins, such as tetrafluoroethylene (TFE), hexafluoropropene (HFP);

$C_2$–$C_8$ hydrogenated fluoroolefins, such as vinyl fluoride (VF), vinylidene fluoride (VDF), trifluoroethylene, $CH_2$=CH—$R_f$ perfluoroalkylethylene, wherein $R_f$ is a $C_1$–$C_6$ perfluoroalkyl, hexafluoroisobutene;

$C_2$–$C_8$ chloro-fluorolefins, such as chlorotrifluoroethylene (CTFE);

$CF_2$=$CFOR_f$ (per) fluoroalkylvinylethers (PAVE), wherein $R_f$ is a $C_1$–$C_6$ (per) fluoroalkyl, for example $CF_3$, $C_2F_5$, $C_3F_7$;

$CF_2$=CFOX (per)fluoro-oxyalkylvinylethers, wherein X is: a $C_1$–$C_{12}$ alkyl, or a $C_1$–$C_{12}$ oxyalkyl, or a $C_1$–$C_{12}$ (per)fluorooxyalkyl having one or more ether groups, for example perfluoro-2-propoxy-propyl;

perfluorodioxoles, such as 2,2,4-trifluoro-5-trifluoromethoxy-1,3-dioxole (TTD), 2,2-bis-trifluoromethyl-4,5-di-fluoro-dioxole (PPD);

sulphonic monomers, such as for example $CF_2$=$CFOCF_2CF_2SO_2F$;

fluorinated dienes as for example
$CF_2$=$CFOCF_2CF_2CF$=$CF_2$,
$CF_2$=$CFOCCl_2CF_2CF$=$CF_2$,
$CF_2$=$CFOCF_2OCF$=$CF_2$,
$CF_2$=$CFOCF_2OCCl$=$CF_2$, $CF_2$=CFOC $(CF_3)_2$ $OCF$=$CF_2$.

The polymerization in aqueous medium can be carried out in suspension, in emulsion or in microemulsion in the presence of the perfluorodiacylperoxides of the invention acting as initiators. The initiator feeding procedures can be in a continuous way or by a single addition at the starting of the polymerization. The amount of perfluorodiacylperoxide initiator is in the range 0.0001%–5% by moles with respect to the amount of the fed monomers. The polymerization temperature can be in the range from –20° C. to 80° C. at pressures comprised between 2 and 50 bar.

In the case of polymerization in aqueous emulsion, the presence of a surfactant is necessary, the fluorinated surfactants such as perfluorooctanoate or mixtures of ammonium, potassium or sodium perfluorooctanoate, perfluorononanoate, perfluorodecanoate are particularly preferred. It is particularly suitable to carry out the polymerization in aqueous phase in the presence of perfluoropolyethers as surfactants. Said perfluoropolyethers can be added to the reaction medium under the form of microemulsion, as described in U.S. Pat. No. 4,864,006.

The present invention will now be better illustrated by the following embodiment Examples, which have a merely indicative purpose but not limitative of the scope of the invention.

EXAMPLES

Example 1
Synthesis of the compound

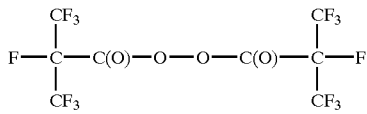

48.7 mmoles of NaOH (1.95 g) which are dissolved in 15 ml of bistilled water are introduced in a four-necked flask equipped with mechanical stirrer, solid $CO_2$ condenser, thermometer and dropping funnel. 50 ml of $CCl_2FCClF_2$ solvent are added and then the temperature of the system is lowered by a cold bath to about 0° C. 4.6 ml of $H_2O_2$ at 57.5% (corresponding to 94 mmoles of $H_2O_2$) are introduced and then, by the dropping funnel, 47 mmoles of $(CF_3)_2CFCOF$ (10.2 g) are introduced. The system temperature passes from 0° C. to 8° C.; the exothermic value of the reaction is controlled by the cold bath, maintaining the temperature at about 2° C. After 10 minutes the flask content is transferred into a separatory funnel and the organic phase is washed with distilled water until a neutral pH, then it is anhydrified with anhydrous $Na_2SO_4$. The peroxide concentration in $CCl_2FCClF_2$ is determined by iodometric titration. The reaction yield is 70%.

Characterization of the Compound $[(CF_3)_2CFCOO]_2$

NMR$^{19}$F spectrum (with respect to $CFCl_{13}$=0) −184 ppm 1 F; −75 ppm 6 F

IR spectrum main bands (cm−1);

intensity: (w)=weak; (m)=mean; (s)=strong; (vs)=very strong:

1853 (m), 1824 (m), 1309 (m), 1264 (s)

Mass spectrum (E.I electronic impact), main peaks and respective intensities:

319 (3), 281 (3), 231 (5), 181 (5), 131 (5), 69 (100)

Decomposition Constants

The thermal decomposition constants $K_d$ (sec$^{-1}$) of the perfluorodiacylperoxide of the invention are determined under anhydrous conditions at different temperatures, equal to 60° C., 70° C., 80° C.

By using as solvent $CCl_2FCClF_2$ and a peroxide concentration equal to 6% by weight, the following results are obtained:

$K_d$=4.4·10$^{-5}$ (60° C.); 16.2·10$^{-5}$ (70° C.); 57.8·10$^{-5}$ (80° C.).

Subsequently it is seen that the decomposition constants, determined at the same temperatures of 60° C., 70° C. and 80° C., introducing 0.5 ml of $H_2O$ per ml of peroxidic solution under magnetic stirring and titrating the organic layer, do not undergo significant variations with respect to the respective above reported thermal decomposition constants.

Besides the pH of the aqueous phase, during the described hydrolytic decomposition, remains unchanged and the only decomposition products are: $CO_2$ and $(CF_3)_2CFCF(CF_3)_2$.

Example 2
Synthesis of the Compound

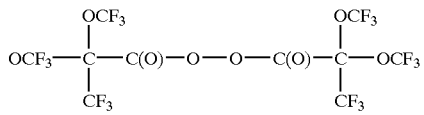

The synthesis procedure is equal to that used in Example 1 with the following quantitative modifications:

26 mmoles of $(CF_3)(CF_3O)_2CCOF$ (7.8 g), 35 mmoles of NaOH (1.39 g), 15 ml of bidistilled water, 3.0 ml of $H_2O_2$ at 57.5% (62 mmoles) and 50 ml of $CCl_2FCClF_2$ solvent.

It is let react for 90 min, following the acylfluoride disappearance by IR analysis. The reaction yield is 46%.

Characterization of the Compound $[(CF_3)(CF_3O)_2CCOO]_2$

NMR$^{19}$F spectrum (with respect to $CFCl_3$=0):

−59 ppm 6 F, −82 ppm 3 F

IR spectrum main bands (cm-1);

intensity: (w)=weak; (m)=mean; (s)=strong; (vs)=very strong:

1854 (m), 1828 (m), 1287 (s), 1254 (s)

Mass spectrum (E.I electronic impact), main peaks and respective intensities:

263 (6), 251 (3), 135 (2), 97 (4), 69 (100)

Decomposition Constants

Decomposition constants $K_d$ (sec$^{-1}$) and respective temperatures determined under anhydrous conditions ($CCl_2FCClF_2$ as solvent):

$K_d$=1.8·10$^{-5}$ (5° C.); 7.6·10$^{-5}$ (15° C.); 46.2·10$^{-5}$ (25° C.).

The decomposition constant in the presence of water is determined at the temperature of 15° C., maintaining under magnetic stirring 8 ml of peroxidic solution and 8 ml of water and titrating the organic layer. No significant variation is noticed with respect to the respective thermal decomposition constant in absence of water.

Example 3
Synthesis of the Compound

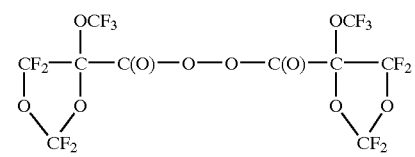

The synthesis procedure is equal to that used in Example 1 with the following quantitative modifications: 23 mmoles of acylfluoride (6.4 g), 25 mmoles of NaOH (0.99 g) 16 ml of bidistilled water, 2.1 ml of $H_2O_2$ at 57.5% (43 mmoles) and 45 ml of $CCl_2FCClF_2$ solvent. The reaction yield is 56%.

Characterization of the Compound

NMR$^{19}$F spectrum (with respect to $CFCl_3$=0):

−55 ppm 1 F, −56 ppm 3 F, −59 ppm IF, −75 ppm 1 F, −90 ppm 1 F

IR spectrum main bands (cm-1);

intensity: (w)=weak; (m)=mean; (s)=strong; (vs)=very strong:

1857 (m), 1828 (m), 1349 (m), 1236 (s) Mass spectrum (E.I electronic impact), main peaks and respective intensities:

229 (42), 163 (21), 135 (7), 116 (3), 97 (30), 78 (4), 69 (100), 50 (6)

Decomposition Constants

Decomposition constants $K_d$ (sec$^{-1}$) and respective temperatures determined under anhydrous conditions (CCl$_2$FCClF$_2$ as solvent):

$K_d$=3.1·10$^{-5}$ (20° C.); 11.7·10$^{-5}$ (30° C.); 50.2·10$^{-5}$ (4° C.).

The decomposition constant in the presence of water is determined at the temperature of 30° C., maintaining under magnetic stirring 8 ml of peroxidic solution and 8 ml of water and titrating the organic layer. No significant variation is noticed with respect to the respective thermal decomposition constant in absence of water.

Example 4

The perfluorodiacylperoxide [(CF$_3$)$_2$CFCOO]$_2$ obtained in Example 1 is used as polymerization initiator in suspension for the preparation of the vinylidene fluoride (VDF) homopolymer.

0.12 mmoles of [(CF$_3$)$_2$CFCOO]$_2$ dissolved in CCl$_2$FCClF$_2$ (1.2 ml) and 20 ml of bidistilled water are introduced into a 50 ml steel reactor, equipped with magnetic stirrer. The so charged reactor is subjected to three cycles reaching the room temperature, condensation in liquid nitrogen, and evacuation at the pressure of 10$^{-3}$ mbar to remove oxygen traces. At the end of these steps 22 atm of VDF are introduced into the reactor and then the system is maintained, under magnetic stirring, at the temperature of 57° C.

When the pressure in the autoclave decreases to 15 atm one provides for the monomer restoration up to the value of 20 atm. After 48 hours the unreacted monomer is removed, obtaining 3.3 g of homopolymer equivalent to a 90% yield.

Example 5 (Comparative)

One proceeds as in Example 4, but using the peroxide having a linear structure [CF$_3$CF$_2$CF$_2$OCF (CF$_3$) CF$_2$OCF (CF$_3$) COO]$_2$ instead of the perfluoroacylperoxide [(CF$_3$)$_2$CFCOO]$_2$ of the invention. While maintaining all the other reaction parameters equal, 0.5 g of VDF homopolymer, equivalent to a yield of 16%, are obtained.

Example 6

The perfluorodiacylperoxide of formula [(CF$_3$O)$_2$(CF$_3$) CCOO]$_2$ obtained in Example 2 is used as polymerization initiator in solution for the preparation of the vinylidene fluoride (VDF) homopolymer.

0.15 mmoles of [(CF$_3$O)$_2$(CF$_3$)CCOO]$_2$ dissolved in CCl$_2$FCClF$_2$ (1.4 ml) and 8.6 ml of perfluoropolyether solvent GALDEN® LS-155 are introduced into a 50 ml steel reactor, equipped with magnetic stirrer. The so charged reactor is subjected to three cycles reaching the room temperature, condensation in liquid nitrogen, and evacuation at the pressure of 10$^{-3}$ mbar to remove oxygen traces. At the end of these steps the reactor is heated to 5° C. and then gaseous VDF is introduced until the monomer dissolved in the solvents is in equilibrium with a pressure of 15 atm of gaseous monomer. The system is maintained, under magnetic stirring, at the temperature of 5° C. for one hour, at the end of which the unreacted monomer is outgassed obtaining, after thermal treatment at 120° C. under vacuum for 5 hours, 3.3 g of VDF homopolymer equivalent to a 65% yield.

Example 7 (Comparative)

One proceeds as in Example 6, but using the peroxide having a linear structure [CF$_3$, CF$_2$CF$_2$OCF(CF$_3$)CF$_2$OCF (CF$_3$)COO]$_2$ instead of the peroxide [(CF$_3$O)$_2$(CF3) CCOO]$_2$ of the invention. While maintaining all the other reaction parameters equal, 1.5 g of VDF homopolymer, equivalent to a 29% yield, are obtained.

Example 8

The peroxide [(CF$_3$)$_2$CFCOO]$_2$ obtained in Example 1 is used as polymerization initiator in emulsion for preparing the VDF homopolymer.

In this and in all the subsequent Examples of polymerization in emulsion, with "emulsifier" a microemulsion salified with sodium is meant, prepared according to U.S. Pat. No. 4,846,006 in the name of the Applicant.

0.106 g of emulsifier and 10.030 g of bidistilled water and then, after a short stirring, 1 ml of a peroxide solution in CCl$_2$FCClF$_2$ solvent containing 0.15 mmoles of [(CF$_3$)$_2$CFCOO]$_2$ are introduced into a 50 ml steel reactor, equipped with magnetic stirrer. The so charged reactor is subjected to two cycles reaching the room temperature, condensation in liquid nitrogen, and evacuation at the pressure of 10$^{-3}$ mbar to remove oxygen traces. At the end of these steps 25 atm of VDF are introduced into the reactor and then the system is maintained, under magnetic stirring, at the temperature of 57° C. After 6 hours the unreacted VDF is outgassed, obtaining 2.1 g of homopolymer equivalent to a 58% yield.

Example 9 (Comparative)

The peroxide having linear structure [CF$_3$CF$_2$CF$_2$COO]$_2$ is used as polymerization initiator in emulsion for preparing the VDF homopolymer.

0.104 g of emulsifier and 10.431 g of bidistilled water and then, after a short stirring, 1 ml of a peroxide solution in CCl$_2$FCClF$_2$ solvent containing 0.15 mmoles of [CF$_3$CF$_2$CF$_2$COO]$_2$ are introduced into a 50 ml steel reactor, equipped with magnetic stirrer. The so charged reactor is subjected to two cycles reaching the room temperature, condensation in liquid nitrogen, and evacuation at the pressure of 10$^{-3}$ mbar to remove oxygen traces. At the end of these steps 25 atm of VDF are introduced into the reactor and then the system is maintained, under magnetic stirring, at the temperature of 57° C. After 6 hours the unreacted VDF is outgassed, obtaining 0.5 g of homopolymer equivalent to a 14% yield.

Example 10

The peroxide [(CF$_3$O)$_2$ (CF$_3$)CCOO]$_2$ obtained in Example 3 is used as polymerization initiator in emulsion for preparing the vinylidene fluoride homopolymer.

0.108 g of emulsifier and 10.042 g of bidistilled water and then, after a short stirring, 1 ml of a peroxide solution in CCl$_2$FCClF$_2$ containing 0.15 mmoles of [(CF$_3$) (CF$_3$O)$_2$ CCOO]$_2$ are introduced into a 50 ml steel reactor, equipped with magnetic stirrer. The so charged reactor is subjected to two cycles reaching the room temperature, condensation in liquid nitrogen, and evacuation at the pressure of 10$^{-3}$ mbar to remove oxygen traces. At the end of these steps 25 atm of VDF are introduced into the reactor and then the system is maintained, under magnetic stirring, at the temperature of 6° C. After 6 hours the unreacted VDF is outgassed, obtaining 2.8 g of homopolymer equivalent to a 78% yield.

Example 11

In a 500 cc Hastelloy autoclave equipped with stirrer working at 800 rpm, after the vacuum has been made, 300 cc of water, 5.3 g per litre of water of an ammonium salified microemulsion prepared according to U.S. Pat. No. 4,864,006 in the name of the Applicant, are introduced in sequence.

Then the autoclave is heated up to 60° C., when it has reached the temperature 65 g of 2,2,3-trifluoro-4-trifluoromethoxy-1,3-dioxole (TTD) are introduced, then tetrafluoroethylene (TFE) is introduced until reaching 9 absolute bar of pressure. 0.6 g of the peroxide $[(CF_3)_2CFCOO]_2$ obtained in Example 1 dissolved in GALDEN® D80 are fed, the solution has a concentration of 0.1 g/cc.

After the reaction starting the pressure is maintained constant by feeding TTD and TFE in a ratio by weight TTD/TFE equal to 18.9. After 220 minutes the reaction is stopped and the latex is discharged.

The product is coagulated with $HNO_3$, the polymer is dried in a stove at 120° C. for 18 hours and then treated at 230° C. for 2 hours.

Charaterization of the TTD/TFE Copolymer

The molar composition of the monomers incorporated into the polymer is: 48% TTD, 52% TFE. All the polymer chain end groups are perfluorinated.

By the infrared spectrum in the absorption zone 1780–1880 it is found the substantial absence of carbonyl and carboxyl groups.

The polymer is amorphous and shows a sole Tg of 106.4° C. at the DSC analysis.

Example 12
Synthesis of the Compound $(c\text{-}C_4F_7COO)_2$

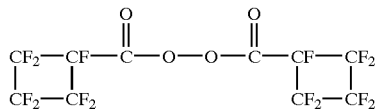

The synthesis procedure is equal to that used in Example 1 with the following quantitative modifications:

30 mmol of c-$C_4F_7$COF (6.8 g), 33 mmol of NaOH (1.32 g), 10 ml of bidistilled water, 6.0 ml of $H_2O_2$, at 30% (60 mmol) and 30 ml of $CCl_2FCClF_2$ solvent. It is let react for 10 minutes, following the acylfluoride disappearance by IR analysis. The reaction yield is 55%.

Characterization of the Compound $(c\text{-}C_4F_7COO)_2$ $^{19}F$ NMR spectrum (with respect to $CFCl_3$=0):
−126 ppm 2 F, −130 ppm 2 F, −131 ppm 2 F, −188 ppm 1 F IR spectrum main bands ($cm^{-1}$):
intensity: (w)=weak; (m)=medium; (s)=strong; (vs)=very strong:
1843 (m), 1817 (m), 1289 (s), 1232 (s)

Mass spectrum (E.I. Electronic Impact), main peaks and respective intensities:
293 (25), 262 (12), 243 (20), 193 (29), 162 (47), 100 (100), 69 (37).

Decomposition Constants

Decomposition constants $K_d$ ($sec^{-1}$) and respective temperatures determined under anhydrous conditions ($CCl_2FCClF_2$ as solvent):
$K_d$=11×10$^{-5}$ (70° C.); 36×10$^{-5}$ (80° C.)

Example 13

The perfluorodiacylperoxide $[(CF_3)_2CFCOO]_2$ obtained in Example 1 is used as polymerization initiator of the TTD (2,2,3-trifluoro-4-trifluorometoxi-1,3-dioxol).

9.3 g (44 mmol) of TTD and 0.044 mmol of $[(CF_3)_2CFCOO]_2$ dissolved in $CCl_2FCClF_2$ are introduced into a 50 ml polymerisation glass reactor, equipped with magnetic stirrer. The so charged reactor is subjected to three cycles reaching the room temperature, condensation in liquid nitrogen and evacuation at the pressure of 10$^{-3}$ mbar to remove oxygen traces. At the end of these steps the system is maintained, under magnetic stirring, at the temperature of 57° C. for 24 hours; then the same quantity of initiator is introduced in the reactor, and the system is let react for 24 hours a second time; the same operations are repeated the third day. After three days at 57° C., the unreacted monomer is removed, keeping the reactor at the temperature of 130° C. and at the pressure of 10$^{-3}$ mbar for one hour. 3,6 g of homopolymer are obtained, equivalent to a 39% yield.

Characterization of TTD homopolymer

DSC: $T_g$=176,1° C.

TGA: −1% 332° C., −2% 356° C., −10% 399° C., −50% 432° C.

Example 14 (Comparative)

One proceeds as in Example 13, but using the peroxide $[CF_3CF_2C(O)O]_2$ instead of the perfluorodiacylperoxide $[(CF_3)_2CFCOO]_2$ of the invention. While maintaining all other reaction parameters equal, except the reaction temperature (which is 27° C.), 0,3 g of TTD homopolymer, equivalent to a yield of 5%, are obtained.

What is claimed is:

1. A polymerization process of one or more fluorinated monomers wherein perfluorodiacylperoxides are used as polymerization initiators, said perfluorodiacylperoxides having the following structures:

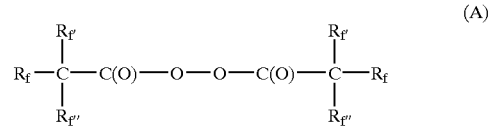

(A)

wherein:
when $R_f$ is F, $R_{f'}$, $R_{f''}$ are both —$CF_3$;
when $R_f$ is —$CF_3$, $R_{f'}$ and $R_{f''}$ are $C_1$–$C_3$ linear or branched perfluorooxvalkyl groups;

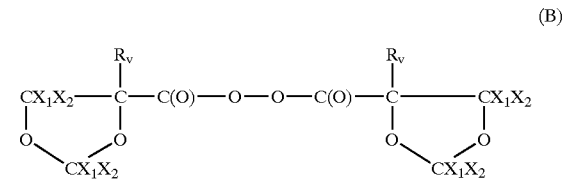

(B)

wherein:
$R_V$ is selected from F, perflurooxyalkyl, $C_1$–$C_3$ linear or branched perfluoroalkyl;
$X_1$, $X_2$ are selected from F, perfluoroalkyl, $C_1$–$C_3$ linear or branched perfluorooxyalkyl;

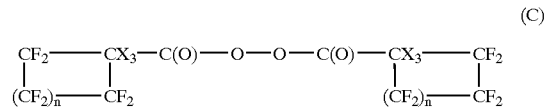

(C)

wherein:
n=1–3

$X_3$ is selected from F, $C_1$-$C_3$ linear or branched perfluoroalkyl, with the proviso that for n=3, $X_3$ cannot be F;

wherein said perfluorodiacyl peroxides meet the following condition: the thermal decomposition constants $K_d$ (sec$^{-1}$) in the presence of water do not undergo substantial variations with respect to the thermal decomposition constants in absence of water.

2. A polymerization process according to claim 1, wherein the polymerization is carried out in aqueous medium, in suspension, in emulsion or in microemulsion.

3. A polymerization process according to claim 1, wherein at temperatures of the order of 50°–80° C., the perfluorodiacylperoxides of structure (C) or the compound of structure (A) having the formula:

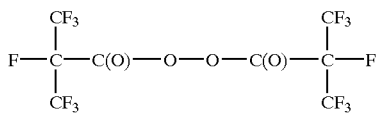

are used.

4. A polymerization process according to claim 1, wherein at temperatures of the order of −20°–+25° C., the perfluorodiacylperoxides of structure (A) of formula:

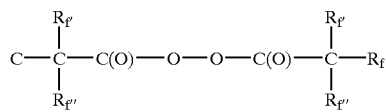

are used, wherein when $R_f$ is —$CF_3$, $R_{f'}$ and $R_{f''}$ are $C_1$-$C_3$ linear or branched perfluorooxyalkyl groups.

5. A polymerization process according to claim 1, wherein the fluorinated monomers are selected from:

$C_2$-$C_8$ perfluoroolefins;

$C_2$-$C_8$ hydrogenated fluoroolefins;

$C_2$-$C_8$ chloro-fluorolefins;

$CF_2$=$CFOR_f$ (per)fluoroalkylvinylethers (PAVE), wherein $R_f$ is a $C_1$-$C_6$ (per)fluoroalkyl;

$CF_2$=CFOX (per)fluoro-oxyalkylvinylethers, wherein X is: a $C_1$-$C_{12}$ alkyl, or a $C_1$-$C_{12}$ oxyalkyl, or a $C_1$-$C_{12}$ (per)fluorooxyalkyl having one or more ether groups;

perfluorodioxoles;

sulphonic monomers;

fluorinated dienes.

6. A polymerization process according to claim 1, wherein the perfluorodiacylperoxide initiator is fed in a continuous way or by a single addition at the starting of the polymerization.

7. A polymerization process according to claim 1, wherein the amount of perfluorodiacylperoxide initiator is in the range 0.0001%–5% by moles with respect to the amount of the fed monomers.

8. A polymerization process according to claim 5, wherein the $C_2$-$C_8$ perfluoroolefins are selected from the group consisting of tetrafluoroethylene (TFE) and hexafluoropropene (HFP).

9. A polymerization process according to claims 5, wherein the $C_2$-$C_8$ hydrogenated fluoroolefins are selected from the group consisting of vinyl fluoride (VF), vinylidene fluoride (VDF), trifluoroethylene, $CH_2$=CH—$R_f$ perfluoroalkylethylene, wherein $R_f$ is a $C_1$-$C_6$ perfluoroalkyl, and hexafluoroisobutene.

10. A polymerization process according to claim 5, wherein the $C_2$-$C_8$ chloro-fluorolefins are chlorotrifluoroethylene (CTFE).

11. A polymerization process according to claim 5, wherein for the $CF_2$=$CFOR_f$ (per)fluoroalkylvinylethers (PAVE), wherein $R_f$ is a $C_1$-$C_6$ (per)fluoroalkyl, the $C_1$-$C_6$ (per)fluoroalkyl is selected from the group consisting of $CF_3$, $C_2F_5$ and $C_3F_7$.

12. A polymerization process according to claim 5, wherein the perfluorodioxoles are selected from the group consisting of 2,2,4-trifluoro-5-trifluoromethoxy-1,3-dioxole (TTD) and 2,2-bis-trifluoromethyl-4,5-difluoro-dioxole (PPD).

13. A polymerization process according to claim 5, wherein the sulphonic monomers are $CF_2$=$CFOCF_2CF_2SO_2F$.

14. A polymerization process according to claim 5, wherein the fluorinated dienes are selected from the group consisting of $CF_2$=$CFOCF_2CF_2CF$=$CF_2$, $CF_2$=$CFOCCl_2CF_2CF$=$CF_2$, $CF_2$=$CFOCF_2OCF$=$CF_2$, $CF_2$=$CFOCF_2OCCl$=$CF_2$, and $CF_2$=$CFOC(CF_3)_2OCF_2$.

* * * * *